United States Patent
Hogan et al.

(10) Patent No.: US 9,109,263 B2
(45) Date of Patent: *Aug. 18, 2015

(54) **COMPOSITIONS TO DETECT *CANDIDA ALBICANS* NUCLEIC ACID**

(75) Inventors: James J. Hogan, Coronado, CA (US); Irene Andruszkiewicz, San Diego, CA (US); Jennifer J. Bungo, San Diego, CA (US); Shannon K. Kaplan, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 605 days.

This patent is subject to a terminal disclaimer.

(21) Appl. No.: 12/843,736

(22) Filed: Jul. 26, 2010

(65) Prior Publication Data

US 2010/0286383 A1 Nov. 11, 2010

Related U.S. Application Data

(60) Continuation of application No. 12/715,132, filed on Mar. 1, 2010, which is a continuation of application No. 12/539,518, filed on Aug. 11, 2009, now Pat. No. 7,670,780, which is a division of application No. 12/335,356, filed on Dec. 15, 2008, now Pat. No. 7,595,164.

(60) Provisional application No. 61/016,777, filed on Dec. 26, 2007.

(51) Int. Cl.
*C12Q 1/68* (2006.01)

(52) U.S. Cl.
CPC .................................. *C12Q 1/6895* (2013.01)

(58) Field of Classification Search
None
See application file for complete search history.

(56) References Cited

U.S. PATENT DOCUMENTS

| | | |
|---|---|---|
| 4,581,333 A | 4/1986 | Kourilsky et al. |
| 4,683,195 A | 7/1987 | Mullis et al. |
| 4,683,202 A | 7/1987 | Mullis |
| 4,800,159 A | 1/1989 | Mullis et al. |
| 4,868,105 A | 9/1989 | Urdea et al. |
| 5,118,801 A | 6/1992 | Lizardi et al. |
| 5,124,246 A | 6/1992 | Urdea et al. |
| 5,130,238 A | 7/1992 | Malek et al. |
| 5,283,174 A | 2/1994 | Arnold, Jr. et al. |
| 5,312,728 A | 5/1994 | Lizardi et al. |
| 5,378,825 A | 1/1995 | Cook et al. |
| 5,399,491 A | 3/1995 | Kacian et al. |
| 5,401,631 A | 3/1995 | Lane et al. |
| 5,403,710 A | 4/1995 | Weisburg et al. |
| 5,422,252 A | 6/1995 | Walker et al. |
| 5,424,413 A | 6/1995 | Hogan et al. |
| 5,427,930 A | 6/1995 | Birkenmeyer et al. |
| 5,437,990 A | 8/1995 | Burg et al. |
| 5,451,503 A | 9/1995 | Hogan et al. |
| 5,516,663 A | 5/1996 | Backman et al. |
| 5,545,525 A | 8/1996 | Montplaisir et al. |
| 5,547,842 A | 8/1996 | Hogan et al. |
| 5,547,861 A | 8/1996 | Nadeau et al. |
| 5,554,516 A | 9/1996 | Kacian et al. |
| 5,585,481 A | 12/1996 | Arnold, Jr. et al. |
| 5,639,604 A | 6/1997 | Arnold, Jr. et al. |
| 5,648,211 A | 7/1997 | Fraiser et al. |
| 5,656,207 A | 8/1997 | Woodhead et al. |
| 5,658,726 A | 8/1997 | Lemontt |
| 5,658,737 A | 8/1997 | Nelson et al. |
| 5,707,802 A | 1/1998 | Sandhu et al. |
| 5,763,169 A | 6/1998 | Sandhu et al. |
| 5,824,518 A | 10/1998 | Kacian et al. |
| 5,849,481 A | 12/1998 | Urdea et al. |
| 5,908,693 A | 6/1999 | Delgado et al. |
| 5,925,517 A | 7/1999 | Tyagi et al. |
| 6,046,006 A | 4/2000 | Einsele et al. |
| 6,150,097 A | 11/2000 | Tyagi et al. |
| 6,180,339 B1 | 1/2001 | Sandhu et al. |
| 6,180,340 B1 | 1/2001 | Nelson |
| 6,235,890 B1 | 5/2001 | Morrison et al. |
| 6,350,579 B1 | 2/2002 | Nelson |
| 6,361,945 B1 | 3/2002 | Becker et al. |
| 6,495,327 B2 | 12/2002 | Milliman et al. |
| 6,534,274 B2 | 3/2003 | Becker et al. |
| 6,605,439 B2 | 8/2003 | Einsele |
| 6,747,137 B1 | 6/2004 | Weinstock et al. |
| 6,821,770 B1 | 11/2004 | Hogan |
| 6,835,542 B2 | 12/2004 | Becker et al. |
| 6,849,412 B2 | 2/2005 | Becker et al. |
| 6,858,387 B1 | 2/2005 | Smith et al. |

(Continued)

FOREIGN PATENT DOCUMENTS

EP 1 239 052 A2 9/2002
JP 2004147550 A 5/2004

(Continued)

OTHER PUBLICATIONS

Lowe et al., A computer program for selection of oligonucleotide primers for polymerase chain reactions. Nucleic Acids Research, vol. 18, No. 7, pp. 1757-1761, 1990.*

(Continued)

*Primary Examiner* — Kenneth Horlick

(74) *Attorney, Agent, or Firm* — Jeffrey E. Landes

(57) ABSTRACT

Compositions are disclosed as nucleic acid sequences that may be used as amplification oligomers, including primers, capture probes for sample preparation, and detection probes specific for *Candida albicans* 26S rRNA sequences or DNA encoding 26S rRNA. Methods are disclosed for detecting the presence of *C. albicans* in samples by using the disclosed compositions in methods that include in vitro nucleic acid amplification of a 26S rRNA sequence or DNA encoding the 26S rRNA sequence to produce a detectable amplification product.

7 Claims, 3 Drawing Sheets

(56) References Cited

U.S. PATENT DOCUMENTS

| | | | |
|---|---|---|---|
| 6,949,367 | B1 | 9/2005 | Dempcy et al. |
| 7,595,164 | B2 | 9/2009 | Hogan et al. |
| 7,670,780 | B2 | 3/2010 | Hogan et al. |
| 2003/0175727 | A1 | 9/2003 | Hyldig-Nielsen et al. |
| 2004/0170954 | A1 | 9/2004 | McKenney et al. |
| 2006/0046265 | A1 | 3/2006 | Becker et al. |
| 2006/0068417 | A1 | 3/2006 | Becker et al. |
| 2006/0194240 | A1 | 8/2006 | Arnold, Jr. et al. |

FOREIGN PATENT DOCUMENTS

| | | | |
|---|---|---|---|
| WO | 88/01302 | A1 | 2/1988 |
| WO | 88/10315 | A1 | 12/1988 |
| WO | 89/10415 | A1 | 11/1989 |
| WO | 93/13121 | A1 | 7/1993 |
| WO | 93/23568 | A1 | 11/1993 |
| WO | 93/23659 | A1 | 12/1993 |
| WO | 95/03430 | A1 | 2/1995 |
| WO | 95/32305 | A1 | 11/1995 |
| WO | 97/36003 | A1 | 10/1997 |
| WO | 00/66789 | A2 | 11/2000 |
| WO | 03/027329 | A1 | 4/2003 |
| WO | 03/095677 | A1 | 11/2003 |
| WO | 2004/044247 | A2 | 5/2004 |
| WO | 2004/046375 | A2 | 6/2004 |
| WO | 2007/023461 | A2 | 3/2007 |
| WO | WO 2007023461 | A2 * | 3/2007 |
| WO | 2007/118222 | A2 | 10/2007 |

OTHER PUBLICATIONS

Rozen et al. Primers on the www for general users and for biologist programmers. In:Misener S, Krawetz SA, editors. Methods in Molecular Biology. Totowa:Humana Press,1999;365-86.*

Buck et al. Design strategies and performance of custom DNA sequencing primers. BioTechniques 1999;27:528-36.*

USPTO Office Action, U.S. Appl. No. 12/715,132, mailed Mar. 15, 2012.

Sambrook et al., Molecular Cloning, A Laboratory Manual, 2nd ed. (Cold Spring Harbor Laboratory Press, Cold Spring Harbor, NY, 1989), §§ 1.90-1.91, 7.37-7.57, 9.47-9.51 and 11.47-11.57, particularly at §§ 9.50-9.51, 11.12-11.13, 11.45-11.47 and 11.55-11.57.

Adams et al., ed., The Biochemistry of the Nucleic Acids 5-36, 1992, 11th ed., Chapman & Hall, New York.

Vester et al., "LNA (Locked Nucleic Acid): High-Affinity Targeting of Complementary RNA and DNA," BioChemistry, 2004, 43(42), pp. 13233-13241, American Chemical Society, Washington D.C.

PCT International Search Report, International Application No. PCT/US2008/86863, Dec. 15, 2008 (Date of Issuance of Report—Jun. 22, 2009).

PCT Written Opinion of the International Searching Authority, International Application No. PCT/US2008/86863, Dec. 15, 2008 (Date of Issuance of Report—Jun. 22, 2009).

PCT International Preliminary Report on Patentability and Written Opinion, International Application No. PCT/US2008/086863, Jul. 8, 2010.

AU Examiner's Report, Australian Patent Application No. 2008343380, dated Oct. 18, 2011.

EPO Office Action, European Patent Application No. 08 868 739.7, Sep. 22, 2011.

Requisition by the Examiner, Canadian Patent Application No. 2,715,991, dated May 31, 2012.

Sandhu G.S. et al., "Molecular proves for diagnosis of fungal infection", Journal of Clinical Microbiology, 33(11), pp. 2913-2919, 1995.

Examination Report, European Patent Application No. 08 868 739.7-2402, mailed Dec. 6, 2012.

Non-Final Rejection, U.S. Appl. No. 12/715,132, mailed Aug. 29, 2014.

Rozen et al. Primers on the WWW for general users and for biologist programmers. In:Misener S, Krawetz SA, editors. Methods in Molecular Biology. Totowa:Humana Press, 1999;365-86.

Bucket al. Design strategies and performance of custom DNA sequencing primers. BioTechniques 1999;27:528-36.

* cited by examiner

```
                           SEQUENCE LISTING

<160> NUMBER OF SEQ ID NOS: 37

<210> SEQ ID NO 1
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 1
cagattcccc ttgtccgtac c                                              21

<210> SEQ ID NO 2
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 2
gacagtcaga ttccccttgt cc                                             22

<210> SEQ ID NO 3
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 3
cacuttctga ccatcacaat gc                                             22

<210> SEQ ID NO 4
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 4
gataaggatt ggctctaagg atcgggtgtc                                     30

<210> SEQ ID NO 5
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 5
aatttaatac gactcactat agggagagat aaggattggc tctaaggatc gggtgtc       57

<210> SEQ ID NO 6
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 6
gcggtgactg ttggcgggct gtttc                                          25
```

<210> SEQ ID NO 7
<211> LENGTH: 52
<212> TYPE: DNA
<213> ORGANISM: Artificial Sequence
<220> FEATURE:
<223> OTHER INFORMATION: Synthetic Oligonucleotide

<400> SEQUENCE: 7
aatttaatac gactcactat agggagagcg gtgactgttg gcgggctgtt tc            52

<210> SEQ ID NO 8
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 8
gctgtttcac gacggactgc tggtggatg                                     29

<210> SEQ ID NO 9
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 9
aatttaatac gactcactat agggagagct gtttcacgac ggactgctgg tggatg       56

<210> SEQ ID NO 10
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 10
ccauaaagac cuaccaagcg ug                                            22

<210> SEQ ID NO 11
<211> LENGTH: 27
<212> TYPE: RNA
<213> ORGANISM: Artificial Sequence
<220> FEATURE:
<223> OTHER INFORMATION: Synthetic Oligonucleotide

<400> SEQUENCE: 11
cacgcccaua aagaccuacc aagcgug                                       27

<210> SEQ ID NO 12
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 12
ccggacggcc auaaagaccu                                               20

<210> SEQ ID NO 13
<211> LENGTH: 25
<212> TYPE: RNA
<213> ORGANISM: Artificial Sequence
<220> FEATURE:
<223> OTHER INFORMATION: Synthetic Oligonucleotide

```
<400> SEQUENCE: 13
ccggacggcc auaaagaccu uccgg                                          25

<210> SEQ ID NO 14
<211> LENGTH: 17
<212> TYPE: RNA
<213> ORGANISM: Artificial Sequence
<220> FEATURE:
<223> OTHER INFORMATION: Synthetic Oligonucleotide

<400> SEQUENCE: 14
cggacggcca uaaagac                                                   17

<210> SEQ ID NO 15
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 15
cggacggcca uaaagacguc cg                                             22

<210> SEQ ID NO 16
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 16
cuuaucccga aguuacggau c                                              21

<210> SEQ ID NO 17
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 17
caccgccgcg ucuacacaag                                                20

<210> SEQ ID NO 18
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 18
gaaacagccc gccaacaguc ac                                             22

<210> SEQ ID NO 19
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 19
ccugcgttat cgtttaacag atgtgcc                                        27

<210> SEQ ID NO 20
```

<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 20
caugagtccc ccttaggaca cctgc                                    25

<210> SEQ ID NO 21
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 21
ggagatttct gttctccatg agtcc                                    25

<210> SEQ ID NO 22
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 22
ggagggtgta gaataagtgg gagcttcg                                 28

<210> SEQ ID NO 23
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 23
aatttaatac gactcactat agggagagga gggtgtagaa taagtgggag cttcg   55

<210> SEQ ID NO 24
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 24
gcttcggcgc cggtgaaata ccactacc                                 28

<210> SEQ ID NO 25
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 25
aatttaatac gactcactat agggagagct tcggcgccgg tgaaatacca ctacc   55

<210> SEQ ID NO 26
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 26

-continued

```
cttattcaat gaagcggagc tggaggtc                                28

<210> SEQ ID NO 27
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 27
aatttaatac gactcactat agggagactt attcaatgaa gcggagctgg aggtc    55

<210> SEQ ID NO 28
<211> LENGTH: 16
<212> TYPE: RNA
<213> ORGANISM: Artificial Sequence
<220> FEATURE:
<223> OTHER INFORMATION: Synthetic Oligonucleotide

<400> SEQUENCE: 28
cccagagggc uuaaug                                             16

<210> SEQ ID NO 29
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 29
cccagagggc uuaaugcugg g                                       21

<210> SEQ ID NO 30
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 30
cggaucgccc agagggcuua                                         20

<210> SEQ ID NO 31
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 31
cggaucgccc agagggcuua auccg                                   25

<210> SEQ ID NO 32
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 32
ccuccauguc uuuucacaau g                                       21

<210> SEQ ID NO 33
<211> LENGTH: 20
<212> TYPE: RNA
```

```
<213> ORGANISM: Artificial Sequence
<220> FEATURE:
<223> OTHER INFORMATION: Synthetic Oligonucleotide

<400> SEQUENCE: 33
gaagcuccca cuuauucuac                                                    20

<210> SEQ ID NO 34
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 34
gaauaaguaa aaaaacuaua g                                                  21

<210> SEQ ID NO 35
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 35
kkkkkkkkkk kkkkkkkk                                                      18

<210> SEQ ID NO 36
<211> LENGTH: 24
<212> TYPE: RNA
<213> ORGANISM: Artificial Sequence
<220> FEATURE:
<223> OTHER INFORMATION: Synthetic Oligonucleotide

<400> SEQUENCE: 36
cgaggcauuu ggcuaccuua agag                                               24

<210> SEQ ID NO 37
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 37
aatttaatac gactcactat agggaga                                            27
```

COMPOSITIONS TO DETECT *CANDIDA ALBICANS* NUCLEIC ACID

CROSS-REFERENCE TO RELATED APPLICATIONS

This application is a continuation of U.S. application Ser. No. 12/715,132, filed Mar. 1, 2010, which is a continuation of U.S. application Ser. No. 12/539,518, filed Aug. 11, 2009, now U.S. Pat. No. 7,670,780, which is a division of U.S. application Ser. No. 12/335,356, filed Dec. 15, 2008, now U.S. Pat. No. 7,595,164, which claims the benefit of U.S. Provisional Application No. 61/016,777, filed Dec. 26, 2007, each of which applications is hereby incorporated by reference herein in its entirety.

FIELD OF THE INVENTION

This invention relates to detection of the presence of fungi in a sample by using molecular biological methods, and specifically relates to detection of *Candida albicans* in a sample by amplifying *C. albicans* nucleic acid sequences and detecting the amplified nucleic acid sequences.

SUMMARY

Disclosed are methods of detecting *Candida albicans* in a sample, including environmental samples, biopharmaceutical samples and biological specimens derived from infected humans, by amplifying and detecting target sequences contained in *C. albicans* 26S rRNA or DNA encoding 26S rRNA. By using specific amplification and detection probe oligomers disclosed herein, the methods amplify target sequences in 26S rRNA sequences of *C. albicans* and detect the amplified products. Some embodiments monitor the development of specific amplification products during the amplification step. Some embodiments include a sample processing step using a capture probe oligomer.

A method is disclosed for detecting *Candida albicans* in a sample, comprising the steps of: mixing a sample that contains a *C. albicans* target nucleic acid that is a 26S rRNA sequence or DNA encoding the 26S rRNA sequence with a first amplification oligomer comprising a target binding region consisting of SEQ ID NO: 1 or SEQ ID NO: 2 and a second amplification oligomer comprising a target binding region consisting of SEQ ID NO: 6; providing an enzyme with nucleic acid polymerase activity and nucleic acid precursors to make an amplification mixture that includes the first and second amplification oligomers and the *C. albicans* target nucleic acid; elongating in vitro a 3' end of at least one of the amplification oligomers hybridized to the *C. albicans* target nucleic acid by using the enzyme with nucleic acid polymerase activity and the *C. albicans* target nucleic acid as a template to produce an amplified product; and, detecting the amplified product by hybridizing the amplified product specifically to a detection probe oligomer comprising a target binding sequence consisting of SEQ ID NO:10 to indicate the presence *Candida albicans* in the sample. Some embodiments also include a sample processing step that captures the *C. albicans* target nucleic acid from the sample before the mixing step. The sample processing step may use a capture probe oligomer that contains a target binding sequence consisting of SEQ ID NO: 35 or 36, wherein the target binding sequence is optionally covalently attached to a 3' tail sequence.

A composition is disclosed for detecting *Candida albicans* 26S rRNA sequence or DNA encoding the 26S rRNA sequence by using in vitro amplification, comprising a first amplification oligomer comprising a target binding region consisting of SEQ ID NO: 1 or SEQ ID NO: 2, a second amplification oligomer comprising a target binding region consisting of SEQ ID NO: 6, and a detection probe oligomer comprising a target binding region consisting of SEQ ID NO: 10. Some embodiments also include at least one capture probe oligomer that contains a target binding region consisting of SEQ ID NO: 35 or 36, optionally with a 3' tail sequence covalently attached to the target binding sequence.

Another method is disclosed for detecting *Candida albicans* in a sample, comprising the steps of: mixing a sample that contains a *C. albicans* target nucleic acid that is a 26S rRNA sequence or DNA encoding the 26S rRNA sequence with a first amplification oligomer comprising a target binding region consisting of SEQ ID NO: 19 and a second amplification oligomer comprising a target binding region consisting of SEQ ID NO: 24; providing an enzyme with nucleic acid polymerase activity and nucleic acid precursors to make an amplification mixture that includes the first and second amplification oligomers and the *C. albicans* target nucleic acid; elongating in vitro a 3' end of at least one of the amplification oligomers hybridized to the *C. albicans* target nucleic acid by using the enzyme with nucleic acid polymerase activity and the *C. albicans* target nucleic acid as a template to produce an amplified product; and, detecting the amplified product by hybridizing the amplified product specifically to a detection probe oligomer comprising a target binding sequence consisting of SEQ ID NO:28 to indicate the presence *Candida albicans* in the sample. Some embodiments also include a sample processing step that captures the *C. albicans* target nucleic acid from the sample before the mixing step. The sample processing step may use a capture probe oligomer that contains a target binding sequence consisting of SEQ ID NO: 35 or 36, wherein the target binding sequence is optionally covalently attached to a 3' tail sequence.

Another composition is disclosed for detecting *Candida albicans* 26S rRNA sequence or DNA encoding the 26S rRNA sequence by using in vitro amplification, comprising a first amplification oligomer comprising a target binding region consisting of SEQ ID NO: 19, a second amplification oligomer comprising a target binding region consisting of SEQ ID NO: 24, and a detection probe oligomer comprising a target binding region consisting of SEQ ID NO: 28. Some embodiments also include at least one capture probe oligomer that contains a target binding region consisting of SEQ ID NO: 35 or 36, optionally with a 3' tail sequence covalently attached to the target binding sequence.

Other methods and compositions are disclosed for amplifying and detecting *Candida albicans* 26S rRNA sequence or DNA encoding the 26S rRNA sequence. The methods and compositions may comprise oligomer combinations of target binding regions for a first amplification oligomer, a second amplification oligomer, and a detection probe oligomer, respectively, as follows: SEQ ID NOs: 1, 4 & 10; SEQ ID NOs: 1, 4 & 12; SEQ ID NOs: 1, 4 & 14; SEQ ID NOs: 2, 4 & 10; SEQ ID NOs: 2, 4 & 12; SEQ ID NOs: 2, 4 & 14; SEQ ID NOs: 3, 4 & 10; SEQ ID NOs: 3, 4 & 12; SEQ ID NOs: 3, 4 & 14; SEQ ID NOs: 1, 6 & 10; SEQ ID NOs: 1, 6 & 12; SEQ ID NOs: 1, 6 & 14; SEQ ID NOs: 2, 6 & 10; SEQ ID NOs: 2, 6 & 12; SEQ ID NOs: 2, 6 & 14; SEQ ID NOs: 3, 6 & 10; SEQ ID NOs: 3, 6 & 12; SEQ ID NOs: 3, 6 & 14; SEQ ID NOs: 1, 8 & 10; SEQ ID NOs: 1, 8 & 12; SEQ ID NOs: 1, 8 & 14; SEQ ID NOs: 2, 8 & 10; SEQ ID NOs: 2, 8 & 12; SEQ ID NOs: 2, 8 & 14; SEQ ID NOs: 3, 8 & 10; SEQ ID NOs: 3, 8 & 12; SEQ ID NOs: 3, 8 & 14; SEQ ID NOs: 19, 22 & 28; SEQ ID NOs:

19, 22 & 30; SEQ ID NOs: 20, 22 & 28; SEQ ID NOs: 20, 22 & 30; SEQ ID NOs: 21, 22 & 28; SEQ ID NOs: 21, 22 & 30; SEQ ID NOs: 19, 24 & 28; SEQ ID NOs: 19, 24 & 30; SEQ ID NOs: 20, 24 & 28; SEQ ID NOs: 20, 24 & 30; SEQ ID NOs: 21, 24 & 28; SEQ ID NOs: 21, 24 & 30; SEQ ID NOs: 19, 26 & 28; SEQ ID NOs: 19, 26 & 30; SEQ ID NOs: 20, 26 & 28; SEQ ID NOs: 20, 26 & 30; SEQ ID NOs: 21, 26 & 28; and, SEQ ID NOs: 21, 26 & 30. The methods and compositions may also comprise at least one capture probe oligomer that contains a target binding region consisting of SEQ ID NO: 35 or 36, optionally with a 3' tail sequence covalently attached to the target binding sequence.

DETAILED DESCRIPTION

Figure 1:
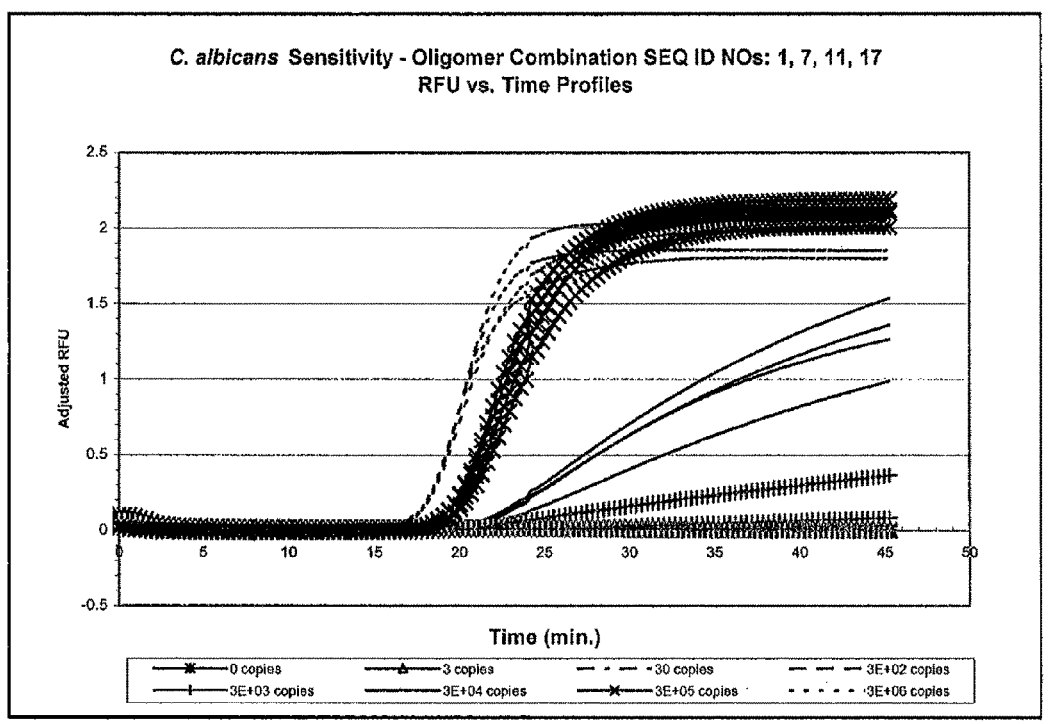
FIG. 1 shows the real-time fluorescent signal that was obtained from amplification of varying copy levels of *C. albicans* 26S rRNA using oligomer combination SEQ ID NOs: 1, 7, 11 & 17 as described in Example 2.

Methods are disclosed for sensitively and specifically detecting the presence of *Candida albicans* in an environmental, biopharmaceutical or biological sample by detecting *C. albicans* nucleic acids. The methods include performing a nucleic acid amplification of 26S rRNA sequences and detecting the amplified product, typically by using a nucleic acid probe that specifically hybridizes to the amplified product to provide a signal that indicates the presence of *C. albicans* in the sample. The amplification step includes contacting the sample with one or more amplification oligomers specific for a target sequence in 26S rRNA to produce an amplified product if *C. albicans* rRNA is present in the sample. Amplification synthesizes additional copies of the target sequence or its complement by using at least one nucleic acid polymerase to extend the sequence from an amplification oligomer (a primer) using a *C. albicans* template strand. Preferred embodiments for detecting the amplified product use a hybridizing step that includes contacting the amplified product with at least one probe specific for an amplified sequence, e.g., a sequence contained in the target sequence that is flanked by a pair of amplification oligomers. The detecting step may be performed after the amplification reaction is completed, or may be performed simultaneous with the amplification reaction (sometimes referred to as "real-time"). In preferred embodiments, the detection step detects the amplified product using a probe that is detected in a homogeneous reaction, i.e., detection of the hybridized probe does not require removal of unhybridized probe from the mixture (e.g., U.S. Pat. Nos. 5,639,604 and 5,283,174, Arnold Jr. et al.). In preferred embodiments that detect the amplified product near or at the end of the amplification step, a linear probe hybridizes to the amplified product to provide a signal that indicates hybridization of the probe to the amplified sequence. In preferred embodiments that use real-time detection, the probe is preferably a hairpin structure probe that includes a reporter moiety that provides the detected signal when the probe binds to the amplified product. For example, a hairpin probe may include a reporter moiety or label, such as a fluorophore ("F"), attached to one end of the probe and an interacting compound, such as quencher ("Q"), attached to the other end the hairpin structure to inhibit signal production when the hairpin structure is in the "closed" conformation and not hybridized to the amplified product, whereas a detectable signal results when the probe is hybridized to a complementary sequence in the amplified product, thus converting the probe to a "open" conformation. Examples of hairpin structure probe include a molecular beacon, molecular torch, or hybridization switch probe and other forms (e.g., U.S. Pat. Nos. 5,118,801 and 5,312,728, Lizardi et al; U.S. Pat. Nos. 5,925,517 and 6,150,097, Tyagi et al.; U.S. Pat. Nos. 6,849,412, 6,835,542, 6,534,274 and 6,361,945, Becker et al.; US Pub. No. 2006-0068417 A1, Becker et al.; and, US Pub. No. 2006-0194240 A1, Arnold Jr. et al.).

To aid in understanding this disclosure, some terms used herein are described below. Unless otherwise described, scientific and technical terms used herein have the same meaning as commonly understood by those skilled in the relevant art based on technical literature, e.g., in *Dictionary of Microbiology and Molecular Biology*, 2nd ed. (Singleton et al., 1994, John Wiley & Sons, New York, N.Y.), *The Harper Collins Dictionary of Biology* (Hale & Marham, 1991, Harper Perennial, New York, N.Y.), or *Dorland's Illustrated Medical Dictionary*, 30$^{th}$ ed. (2003, W.B. Saunders, Elsevier Inc., Philadelphia, Pa.). Unless otherwise described, techniques employed or contemplated herein are standard methods well known in the art of molecular biology.

"Sample" includes any specimen that may contain *Candida* fungi or components thereof, such as nucleic acids or nucleic acid fragments. Samples may be obtained from environmental sources, e.g., water, soil, slurries, debris, biofilms from containers of aqueous fluids, airborne particles or aerosols, and the like, which may include processed samples, such as those obtained from passing an environmental sample over or through a filter, by centrifugation, or by adherence to a medium, matrix, or support. Samples may also be obtained from any step along a food supply chain to support food product safety or any step along a biopharmaceutical process stream to support sterile product development. "Biological samples" include any tissue or material derived from a living or dead mammal, including humans, which may contain *Candida* or target nucleic acid derived therefrom, e.g., respiratory tissue or exudates such as bronchoscopy, bronchoalveolar lavage (BAL) or lung biopsy, sputum, peripheral blood, plasma, serum, lymph node, gastrointestinal tissue, urine, exudates, or other body fluids. A sample may be treated to physically or mechanically disrupt aggregates or cells to release intracellular components, including nucleic acids, into a solution which may contain other components, such as enzymes, buffers, salts, detergents and the like.

"Nucleic acid" refers to a multimeric compound comprising nucleosides or nucleoside analogs which have nitrogenous heterocyclic bases, or base analogs, which are linked by phosphodiester bonds or other linkages to form a polynucleotide. Nucleic acids include RNA, DNA, or chimeric DNA-RNA polymers, and analogs thereof. A nucleic acid "backbone" may be made up of a variety of linkages, including one or more of sugar-phosphodiester linkages, peptide-nucleic acid (PNA) bonds (PCT No. WO 95/32305), phosphorothioate linkages, methylphosphonate linkages, or combinations thereof. Sugar moieties of the nucleic acid may be either ribose or deoxyribose, or similar compounds having known substitutions, e.g., 2' methoxy substitutions and 2' halide substitutions (e.g., 2'-F). Nitrogenous bases may be conventional bases (A, G, C, T, U), analogs thereof (e.g., inosine; *The Biochemistry of the Nucleic Acids* 5-36, Adams et al., ed., 11$^{th}$ ed., 1992), derivatives of purine or pyrimidine bases, e.g., N$^4$-methyl deoxyguanosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, O$^6$-methylguanine, 4-thio-pyrimidines, 4-amino-pyrimidines, 4-dimethylhydrazine-pyrimidines, and O$^4$-alkyl-pyrimidines, and pyrazolo-compounds, such as unsubstituted or 3-substituted pyrazolo[3,4-d]pyrimidine (U.S. Pat. Nos. 5,378,825, 6,949, 367 and PCT No. WO 93/13121). Nucleic acids may include "abasic" positions in which the backbone does not include a nitrogenous base for one or more residues (U.S. Pat. No. 5,585,481). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Nucleic acids also include "locked nucleic acids" (LNA), an analogue containing one or more LNA nucleotide monomers with a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., 2004, *Biochemistry* 43(42): 13233-41). Methods for synthesizing nucleic acids in vitro are well known in the art.

The interchangeable terms "oligomer" and "oligonucleotide" refer to a nucleic acid having generally less than 1,000 nucleotides (nt), including polymers in a range having a lower limit of about 2 nt to 5 nt and an upper limit of about 500 nt to 900 nt. Preferred oligomers are in a size range having a lower limit of about 5 nt to 15 nt and an upper limit of about 50 nt to 600 nt, and particularly preferred embodiments are in a range having a lower limit of about 10 nt to 20 nt and an upper limit of about 22 nt to 100 nt. Preferred oligomers are synthesized by using any well known enzymatic or chemical method and purified by standard methods, e.g., chromatography.

An "amplification oligomer" is an oligonucleotide that hybridizes to a target nucleic acid, or its complement, and participates in a nucleic acid amplification reaction. An example of an amplification oligomer is a "primer" that hybridizes to a template nucleic acid and contains a 3' hydroxyl end that is extended by a polymerase in an amplification process. Another example is an oligonucleotide that participates in or facilitates amplification but is not extended by a polymerase, e.g., because it has a 3' blocked end. Preferred size ranges for amplification oligomers include those that are about 10 to about 60 nt long and contain at least about 10 contiguous bases, and more preferably at least 12 contiguous bases that are complementary to a region of the target nucleic acid sequence (or its complementary sequence). The contiguous bases are preferably at least 80%, more preferably at least 90%, and most preferably about 100% complementary to the target sequence to which the amplification oligomer binds. An amplification oligomer may optionally include modified nucleotides or analogs, or optionally an additional sequence that participates in an amplification reaction but is not complementary to or contained in the target or template sequence. For example, a "promoter-primer" is an oligonucleotide that includes a 5' promoter sequence that is non-complementary to the target nucleic acid but is adjacent or near to the target complementary sequence of the primer. Those skilled in the art will understand that an amplification oligomer that functions as a primer may be modified to include a 5' promoter sequence, and thus function as a promoter-primer, and a promoter-primer can function as a primer independent of its promoter sequence, i.e., the oligonucleotide may be modified by removal of, or synthesis without, its promoter sequence. An amplification oligomer referred to as a "promoter-provider" includes a promoter sequence that serves as a template for polymerization but the oligonucleotide is not extended from its 3' end which is blocked and, therefore, not available for extension by polymerase activity.

"Amplification" refers to any known in vitro procedure for obtaining multiple copies of a target nucleic acid sequence or fragments thereof, or its complementary sequence. Amplification of "fragments" refers to production of an amplified nucleic acid that contains less than the complete target nucleic acid or its complement, e.g., by using an amplification oligonucleotide that hybridizes to and initiates polymerization from an internal position of the target nucleic acid. Known amplification methods include, for example, replicase-mediated amplification, the polymerase chain reaction (PCR), ligase chain reaction (LCR), strand displacement amplification (SDA), and transcription-mediated or transcription-associated amplification. Replicase-mediated amplification uses self-replicating RNA molecules, and a replicase such as Qβ-replicase (e.g., U.S. Pat. No. 4,786,600, Kramer et al.). PCR amplification uses a DNA polymerase, pairs of primers, and thermal cycling to synthesize multiple copies of two complementary strands of a dsDNA or from a cDNA (e.g., U.S. Pat. Nos. 4,683,195, 4,683,202 and 4,800,159, Mullis et al.). LCR amplification uses four or more different oligonucleotides to amplify a target and its complementary strand by using multiple cycles of hybridization, ligation, and denaturation (e.g., U.S. Pat. No. 5,427,930, Birkenmeyer et al.; U.S. Pat. No. 5,516,663, Backman et SDA uses a primer that contains a recognition site for a restriction endonuclease and an endonuclease that nicks one strand of a hemimodified DNA duplex that includes the target sequence, whereby amplification occurs in a series of primer extension and strand displacement steps (e.g., U.S. Pat. No. 5,422,252, Walker et al.; U.S. Pat. No. 5,547,861, Nadeau et al.; U.S. Pat. No. 5,648,211, Fraiser et al.).

"Transcription-associated amplification" or "transcription-mediated amplification" (TMA) refers to any type of nucleic acid amplification that uses an RNA polymerase to produce multiple RNA transcripts from a nucleic acid template. These methods generally use an RNA polymerase, a DNA polymerase, nucleic acid substrates (dNTPs and rNTPs), and a template complementary oligonucleotide that includes a promoter sequence, and optionally may include one or more other oligonucleotides. Variations of transcription-associated amplification are well known in the art (e.g., disclosed in detail in U.S. Pat. Nos. 5,399,491 and 5,554,516, Kacian et al.; U.S. Pat. No. 5,437,990, Burg et al.; PCT Nos. WO 88/01302 and WO 88/10315, Gingeras et al.; U.S. Pat. No. 5,130,238, Malek et al.; U.S. Pat. Nos. 4,868,105 and 5,124,246, Urdea et al.; PCT No. WO 95/03430, Ryder et al.; and, US Pub. No. 2006-0046265 A1, Becker et al.). TMA methods of Kacian et al. and a one primer transcription-associated method (US Pub. No. 2006-0046265 A1, Becker et al.) are preferred embodiments of transcription-associated amplification methods for use in detection of *Candida* target sequences as described herein. Although preferred embodiments are illustrated by such amplification reactions, a person of ordinary skill in the art will appreciated that amplification oligomers disclosed herein may be readily used in other amplification methods that extend a sequence from primer(s) by using a polymerase.

"Probe" refers to a nucleic acid oligomer that hybridizes specifically to a target sequence in a nucleic acid, preferably in an amplified nucleic acid, under conditions that allow hybridization to permit detection of the target sequence or amplified nucleic acid. Detection may either be direct (i.e., probe hybridized directly to its target sequence) or indirect (i.e., probe linked to its target via an intermediate molecular structure). A probe's "target sequence" generally refers to a subsequence within a larger sequence (e.g., a subset of an amplified sequence) that hybridizes specifically to at least a portion of a probe by standard base pairing. A probe may include target-specific sequence and other sequences that contribute to the probe's three-dimensional conformation (e.g., described in U.S. Pat. Nos. 5,118,801 and 5,312,728, Lizardi et al; U.S. Pat. Nos. 6,849,412, 6,835,542, 6,534,274 and 6,361,945, Becker et al.; and, US Pub. No. 2006-0068417 A1, Becker et al.).

By "sufficiently complementary" is meant a contiguous sequence that is capable of hybridizing to another sequence by hydrogen bonding between a series of complementary bases, which may be complementary at each position in the sequence by standard base pairing (e.g., G:C, A:T or A:U pairing) or may contain one or more positions, including abasic ones, which are not complementary bases by standard hydrogen bonding. Contiguous bases are at least 80%, preferably at least 90%, and more preferably about 100% complementary to a sequence to which an oligomer is intended to specifically hybridize. Sequences that are "sufficiently complementary" allow stable hybridization of a nucleic acid oligomer to its target sequence under the selected hybridization conditions, even if the sequences are not completely complementary. Appropriate hybridization conditions are well known in the art, can be predicted readily based on base sequence composition, or can be determined by using routine testing (e.g., Sambrook et al., *Molecular Cloning, A Laboratory Manual*, 2nd ed. (Cold Spring Harbor Laboratory Press, Cold Spring Harbor, N.Y., 1989), §§1.90-1.91, 7.37-7.57, 9.47-9.51 and 11.47-11.57, particularly at §§9.50-9.51, 11.12-11.13, 11.45-11.47 and 11.55-11.57).

"Sample preparation" refers to any steps or methods that prepare a sample for subsequent amplification and detection of *Candida* nucleic acids present in the sample. Sample preparation may include any known method of concentrating components from a larger sample volume or from a substantially aqueous mixture, e.g., by filtration or trapping of airborne particles from an air sample or microbes from a water sample. Sample preparation may include lysis of cellular components and removal of debris, e.g., by filtration or centrifugation, and may include use of nucleic acid oligomers to selectively capture the target nucleic acid from other sample components.

A "capture probe" or "capture oligomer" refers to at least one nucleic acid oligomer that joins a target sequence and an immobilized oligomer by using base pair hybridization to specifically or non-specifically capture the target sequence. A preferred capture probe embodiment includes two binding regions: a target sequence-binding region and an immobilized probe-binding region, usually on the same oligomer, although the two regions may be present on different oligomers joined by one or more linkers. For example, a first oligomer may include the immobilized probe-binding region and a second oligomer may include the target sequence-binding region, and the two different oligomers are joined by a linker that joins the two sequences into a functional unit. Examples of non-specific target capture are described in U.S. application Ser. No. 11/832,367, Becker et al.

An "immobilized probe" or "immobilized nucleic acid" refers to a nucleic acid that joins, directly or indirectly, a capture oligomer to an immobilized support. A preferred immobilized probe is an oligomer joined to a support that facilitates separation of bound target sequence from unbound material in a sample. Supports may include known materials, such as matrices and particles free in solution, e.g., made up of nitrocellulose, nylon, glass, polyacrylate, mixed polymers, polystyrene, silane, polypropylene, metal and preferred embodiments are magnetically attractable particles. Preferred supports are monodisperse magnetic spheres (e.g., uniform size ±5%), to which an immobilized probe is joined directly (via covalent linkage, chelation, or ionic interaction), or indirectly (via one or more linkers), where the linkage or interaction between the probe and support is stable during hybridization conditions.

"Separating" or "purifying" means that one or more components of a mixture, such as a sample, are removed or separated from one or more other components. Sample components include target nucleic acids in a generally aqueous mixture (solution phase), which may include cellular fragments, proteins, carbohydrates, lipids, and other nucleic acids. Separating or purifying removes at least 70%, preferably at least 80%, and more preferably about 95% of the target nucleic acid from other mixture components.

A "label" refers to a molecular moiety or compound that is detected or leads to a detectable signal. A label may be joined directly or indirectly to a nucleic acid probe. Direct labeling can occur through bonds or interactions that link the label to the probe, including covalent bonds or non-covalent interactions, e.g., hydrogen bonds, hydrophobic and ionic interactions, or formation of chelates or coordination complexes. Indirect labeling can occur through use of a bridging moiety or linker (e.g., antibody or additional oligomer), which is either directly or indirectly labeled, and which may amplify the detectable signal. Labels include any detectable moiety, such as a radionuclide, ligand (e.g., biotin, avidin), enzyme, enzyme substrate, reactive group, chromophore (e.g., dye, particle, or bead that imparts detectable color), luminescent compound (e.g., bioluminescent, phosphorescent, or chemiluminescent labels), or fluorophore. Preferred labels include a "homogeneous detectable label" that provides a detectable signal in a homogeneous reaction in which bound labeled probe in a mixture exhibits a detectable change that differs from that of unbound labeled probe, e.g., stability or differential degradation (e.g., U.S. Pat. No. 5,283,174, Arnold et al.; U.S. Pat. No. 5,656,207, Woodhead et al.; U.S. Pat. No. 5,658,737, Nelson at al.). Preferred labels include chemiluminescent compounds, preferably acridinium ester ("AE") compounds that include standard AE and derivatives thereof (described in U.S. Pat. Nos. 5,656,207, 5,658,737 and 5,639,604). Methods of synthesis and attaching labels to nucleic acids and detecting signals from labels are well known (e.g., Sambrook et al., *Molecular Cloning, A Laboratory Manual*, 2nd ed. (Cold Spring Harbor Laboratory Press, Cold Spring Harbor, N.Y., 1989), Chpt. 10; U.S. Pat. Nos. 5,658,737, 5,656,207, 5,547,842, 5,283,174, and 4,581,333).

Methods are disclosed for amplifying and detecting *Candida* nucleic acid, specifically *C. albicans* 26S rRNA sequences or DNA encoding 26S rRNA. Disclosed are selected oligonucleotide sequences that specifically recognize target sequences of *C. albicans* 26S rRNA or their complementary sequences, or DNA encoding 26S rRNA. Such oligonucleotides may function as amplification oligomers, e.g., as primers, promoter-primers, blocked oligomers, and promoter-provider oligomers, whose functions are known (e.g., described in U.S. Pat. Nos. 4,683,195, 4,683,202, 4,800,159, 5,399,491, 5,554,516 and 5,824,518; and, US Pub. No. 2006-0046265 A1). Other embodiments may function as probes to detect the amplified *C. albicans* sequences.

Amplification methods that use transcription-mediated amplification (TMA) include the steps summarized herein (described in detail in U.S. Pat. Nos. 5,399,491, 5,554,516 and 5,824,518). The target nucleic acid that contains the sequence to be amplified is provided as single-stranded nucleic acid (e.g., ssRNA or ssDNA) or made single-stranded by conventional methods, e.g., temperature and/or chemical melting of double-stranded nucleic acid to provide a single-stranded target nucleic acid. A promoter-primer binds specifically to its target sequence in the target nucleic acid and an enzyme with reverse transcriptase (RT) activity extends the 3' end of the promoter-primer using the target strand as a template to make a cDNA of the target sequence, which is in an RNA:DNA duplex. Enzymatic RNase activity (e.g., RNaseH) digests the RNA strand of the RNA:DNA duplex and a second primer binds specifically to its target sequence on the cDNA strand downstream from the promoter-primer end. The RT synthesizes a new DNA strand by extending the 3' end of the second primer using the first cDNA as a template to make a dsDNA that contains a functional promoter sequence. An RNA polymerase specific for the promoter sequence then initiates transcription to produce multiple RNA transcripts that are, e.g., about 100 to 1000 amplified copies ("amplicons") of the initial target strand in the reaction. Amplification continues when the second primer binds specifically to its target sequence in each amplicon and RT makes a DNA copy from the amplicon RNA template to produce an RNA:DNA duplex. RNase in the reaction digests the amplicon RNA from the RNA:DNA duplex and the promoter-primer binds specifically to its complementary sequence in the newly synthesized DNA. The RT extends the 3' end of the promoter-primer to create a dsDNA that contains a functional promoter to which the RNA polymerase binds to transcribe additional amplicons that are complementary to the initial target strand. These autocatalytic reactions make more amplicons repeatedly during the complete amplification reaction, resulting in about a billion-fold amplification of the target sequence that was present in the sample. The amplified products may be detected during amplification, i.e., in real-time, or at completion of the amplification reaction by using a probe that binds specifically to a target sequence in the amplified products. Signal detected from the bound probes indicates the presence of the target nucleic acid in the sample.

Another transcription-associated amplification method summarized herein uses one primer and one or more additional amplification oligomers to amplify nucleic acids in vitro by making transcripts (amplicons) that indicate the presence of the target nucleic acid in a sample (described in detail in US Pub. No. 2006-0046265 A1, Becker et al.). Briefly, this single-primer method uses a primer or "priming oligomer", a "promoter-provider" oligomer that is modified to prevent synthetic extension from its 3' end (typically, by including a 3'-blocking moiety) and, optionally, a binding molecule (e.g., a 3'-blocked extender oligomer) to terminate elongation of a cDNA from the target strand. This method includes the steps of binding the target RNA that contains the target sequence with a primer and, optionally, a binding molecule. The primer hybridizes to the 3' end of the target strand and enzymatic RT activity initiates primer extension from the 3' end of the primer to produce a cDNA, to make a duplex of the new strand and the target strand (RNA:cDNA duplex). When a binding molecule is included in the reaction, such as a 3'-blocked oligomer, it binds to the target strand next to the 5' end of the target sequence to be amplified. When the primer is extended by DNA polymerase activity of RT to produce the cDNA strand, polymerization stops when the primer extension product reaches the binding molecule on the target strand and, thus, the 3' end of the cDNA is determined by the position of the binding molecule on the target strand, making the 3' end of the cDNA complementary to the 5' end of the target sequence. The RNA:cDNA duplex is separated, e.g., by RNase H degradation of the RNA strand, or by using conventional strand separation methods. Then, the promoter-provider oligomer hybridizes to the cDNA strand near its 3' end. The promoter-provider oligomer includes a 5' promoter sequence, a 3' region complementary to a sequence in the 3' region of the cDNA, and a modified 3' end that includes a blocking moiety to prevent initiation of DNA synthesis from the 3' end of the promoter-provider oligomer. In the duplex made of the promoter-provider oligomer and the cDNA strand, the 3'-end of the cDNA is extended by DNA polymerase activity of the RT enzyme, using the promoter oligomer as a template to add a promoter sequence to the cDNA, to make a functional double-stranded promoter. An RNA polymerase specific for the functional promoter sequence then binds to the promoter and transcribes RNA transcripts complementary to the cDNA which are substantially identical to the target region sequence that was amplified from the initial target strand. The amplified RNA transcripts then serve as substrates in the amplification process by binding the primer and serving as a template for further cDNA production. This method ultimately produces many amplicons from the initial target nucleic acid present in the sample, i.e., it makes multiple copies of the target sequence. In embodiments of the method that do not include the binding molecule, the cDNA made from the primer has an indeterminate 3' end, but the other steps proceed as described above.

Detection of the amplified products may be accomplished by a variety of methods. The amplified nucleic acids may be associated with a surface to produce a detectable physical change, such as an electrical signal. Amplified nucleic acids may be concentrated in or on a matrix and detected by detecting a signal from the concentrated nucleic acid or an associated dye (e.g., an intercalating agent such as ethidium bromide or cyber green). Nucleic acids in solution may be detected by detecting an increased dye association in the solution phase. Preferred embodiments detect nucleic acid probes that are complementary to a sequence in the amplified product and form a probe:amplified product complex that provides a detectable signal (e.g., U.S. Pat. Nos. 5,424,413 and 5,451,503, Hogan et al.; and, U.S. Pat. No. 5,849,481, Urdea et al.). Directly or indirectly labeled probes that specifically associate with the amplified product provide a detectable signal to indicate the presence of the target nucleic acid in the sample. For example, if a sample contains a target nucleic acid that is *Candida albicans* 26S rRNA, the amplified product contains the target sequence in or a complementary sequence of the *C. albicans* 26S rRNA, and the probe binds directly or indirectly to the amplified product's target sequence to produce a signal that indicates the presence of *C. albicans* in the sample.

Preferred probe embodiments that hybridize specifically to the amplified product sequences may be oligomers of DNA, RNA, or a mixture of DNA and RNA nucleotides, which may be synthesized with a modified backbone, e.g., a synthetic oligonucleotide that includes one or more 2'-methoxy substituted RNA groups. Probes for detection of amplified *Candida* rRNA sequences may be unlabeled and detected indirectly (e.g., by binding to another binding partner that is detected) or may be labeled with a label that results in a detectable signal. Preferred embodiments include label compounds that emit a detectable light signal, e.g., fluorophores or luminescent compounds detected in a homogeneous mixture. A probe may include more than one label and/or more than one type of label, or detection may rely on using a mixture of probes in which each probe is labeled with a compound that produces a detectable signal (e.g., U.S. Pat. Nos. 6,180,340 and 6,350, 579). Labels may be attached to a probe by any of a variety of known means, e.g., covalent linkages, chelation, and ionic interactions, but preferred embodiments covalently link the label to the oligonucleotide. Probes may be substantially linear oligonucleotides, i.e., lacking conformations held by intramolecular bonds, or may be include functional conformational structures, i.e., conformations such those found in hairpin structure probes held together by intramolecular hybridization. Preferred embodiments of linear oligomers generally include a chemiluminescent label, preferably an AE compound.

Hairpin probes are preferably labeled with any of a variety of different types of interacting labels, in which one interacting member is usually attached to the 5' end of the probe and the other interacting member is attached to the 3' end of the probe. Such interacting members include those often referred to as a reporter dye/quencher pair, a luminescent/quencher pair, luminescent/adduct pair, Forrester energy transfer pair, or dye dimer. A luminescent/quencher pair may be made up of one or more luminescent labels, such as chemiluminescent or fluorescent labels, and one or more quenchers. In preferred embodiments, a hairpin probe is labeled at one end with a fluorophore ("F") that absorbs light at a particular first wavelength or range and emits light at a second emission wavelength or range and labeled at the other end with a quencher ("Q") that dampens, partially or completely, signal emitted from the excited F when Q is in proximity with the fluorophore. Such a hairpin probe may be referred to as labeled with a fluorescent/quencher (F/Q) pair. Fluorophores are well known compounds that include, e.g., acridine, fluorescein, sulforhodamine 101, rhodamine, 5-(2'-aminoethyl)aminoaphthaline-1-sulfonic acid (EDANS), Texas Red, Eosine, Bodipy and lucifer yellow (Tyagi et al., Nature Biotechnology 16:49-53, 1998). Quenchers are well known and include, e.g., 4-(4'-dimethyl-amino-phenylaxo)benzoic acid (DABCYL), thallium, cesium, and p-xylene-bis-pyridinium bromide. Different F/Q combinations are known and many combinations may function together, e.g., DABCYL with fluorescein, rhodamine, or EDANS. Other combinations of labels for hairpin probes include a reporter dye, e.g., FAM™, TET™, JOE™, VIC™ combined with a quencher such as TAMRA™ or a non-fluorescent quencher. A functional F/Q combination may be determined by using routine testing using known procedures.

A preferred embodiment of a hairpin probe is a "molecular torch" that detects an amplified product to indicate the presence of a target *Candida* sequence in a sample after the amplification step. A molecular torch includes: (1) a target detection means that hybridizes to the target sequence, resulting in an open conformation; (2) a torch closing means that hybridizes to the target detecting means in the absence of the target sequence, resulting in a closed conformation; and (3) a joining means that joins the target detection means and the torch closing means (described in detail in U.S. Pat. Nos. 6,849,412, 6,835,542, 6,534,274 and 6,361,945). A torch probe in open conformation results in a detectable signal that indicates the presence of the amplified target sequence, whereas the closed conformation produces an amount of signal that is distinguishable from that of the open conformation indicating that the target sequence is not present. Another preferred hairpin probe embodiment is a "molecular beacon" that includes a label on one arm of the hairpin sequence, a quencher on the other arm, and a loop region joining the two arms (described in detail in U.S. Pat. Nos. 5,118,801 and 5,312,728). Methods for using such hairpin probes are well known in the art.

Oligomers that are not extended by a nucleic acid polymerase include a blocker group that replaces the 3' OH to prevent enzyme-mediated extension of the oligomer in an amplification reaction. Blocked amplification oligomers and/or blocked detection probes present during amplification (for real-time detection) preferably lack a 3' OH but include one or more blocking groups located at or near the 3' end. A blocking group is covalently attached to the 3' terminus of the oligonucleotide or is located near the 3' end, preferably within five residues of the 3' end, and is sufficiently large to limit binding of a polymerase to the oligomer. Many different chemical groups may be used as a blocking moiety, e.g., alkyl groups, non-nucleotide linkers, alkane-diol dideoxynucleotides, and cordycepin.

A preferred method for detection of *Candida albicans* sequences uses a transcription-associated amplification with a hairpin probe, e.g. molecular torch or molecular beacon, because the probe may be added before amplification, and detection is carried out without further addition of reagents. For example, a probe may be designed so that the $T_m$ of the hybridized arms of the hairpin probe (e.g., target binding domain:target closing domain complex of a molecular torch) is higher than the amplification reaction temperature to prevent the probe from prematurely binding to amplified target sequences. After an interval of amplification, the mixture is heated to open the torch probe arms and allow the target binding domain to hybridize to its target sequence in the amplified product. The solution is then cooled to close probes not bound to amplified products, which closes the label/quencher (F/Q) pair, allowing detection of signals from probes hybridized to the amplified target sequences in a homogeneous reaction. For example, the mixture containing the F/Q labeled hairpin probe is irradiated with the appropriate excitation light and the emission signal is measured.

In other embodiments, the hairpin detection probe is designed so that amplified products preferentially hybridize to the target binding domain of the probe during amplification, thereby changing the hairpin from its closed to open conformation as amplification progresses. The amplification reaction mixture is irradiated at intervals during the amplification reaction to detect the emitted signal from the open probes during amplification, i.e., in real-time.

Preparation of samples for amplification of *Candida* sequences may include separating and/or concentrating organisms contained in a sample from other sample components, e.g., filtration of particulate matter from air, water or other types of samples. Sample preparation may also include chemical, mechanical, and/or enzymatic disruption of cells to release intracellular contents, including *Candida* 26S rRNA or DNA encoding the 26S rRNA. Sample preparation may include a step of target capture to specifically or non-specifically separate the target nucleic acids from other sample components. Non-specific target preparation methods may selectively precipitate nucleic acids from a substantially aqueous mixture, adhere nucleic acids to a support that is washed to remove other sample components, or use other means to physically separate nucleic acids, including *Candida* nucleic acid, from a mixture that contains other components. Other non-specific target preparation methods may selectively separate RNA, including *Candida* 26S rRNA, from DNA in a sample.

In a preferred embodiment, *Candida* 26S rRNA or DNA encoding 26S rRNA are selectively separated from other sample components by specifically hybridizing the *Candida* nucleic acid to a capture oligomer specific for the *Candida* target sequence to form a target sequence:capture probe complex that is separated from sample components. A preferred embodiment of specific target capture binds the *Candida* target:capture probe complex to an immobilized probe to form a target:capture probe:immobilized probe complex that is separated from the sample and, optionally, washed to remove non-target sample components. The capture probe includes a sequence that specifically binds to the *Candida* target sequence in 26S rRNA or in DNA encoding 26S rRNA and also includes a specific binding partner that attaches the capture probe with its bound target sequence to a support (e.g., matrix or particle), which facilitates separating the target sequence from the sample components. In a preferred embodiment, the specific binding partner of the capture probe is a 3' tail sequence that is not complementary to the *Candida* target sequence but that hybridizes to a complementary sequence on an immobilized probe attached to the support. Preferred 3' tail sequences are substantially homopolymeric 10 to 40 nt sequences (e.g., $A_{10}$ to $A_{40}$) that bind to a complementary immobilized sequence (e.g., poly-T) attached to the support. Target capture occurs in a solution phase mixture that contains capture oligomers that hybridize specifically to the *Candida* target nucleic acid under hybridizing conditions, usually at a temperature higher than the $T_m$ of the tail sequence:immobilized probe sequence duplex. The *Candida* target:capture probe complex is captured by adjusting the hybridization conditions so that the capture probe tail then hybridizes to the immobilized probe, and the entire complex on the support is separated from the other sample components. The support with the attached complex that includes the *Candida* target sequence may be washed to further remove other sample components. Preferred supports are particulate, such as paramagnetic beads, so that particles with the complex that includes the captured *Candida* target sequence may be suspended in a washing solution and retrieved from the washing solution by using magnetic attraction. In other embodiments, the capture probe may bind nonspecifically to nucleic acids in the sample, including the *Candida* target sequence, and then similar steps of attaching the capture probe:nucleic acid complexes to a support and separating the captured complexes on the support are performed. Whether target capture is specific or non-specific for the *Candida* target sequence, the captured nucleic acids are then subjected to in vitro amplification specific for the intended *Candida* target sequence. To limit the number of handling steps, *Candida* target nucleic acid may be amplified by mixing the *Candida* target sequence in the captured complex on the support with amplification reagents, or a primer may be included in the target capture reaction mixture, thus allowing the *Candida* specific primer and target sequences to hybridize during target capture and be separated together from the sample in the captured complex.

Assays for detection of *Candida* nucleic acid may optionally include a non-Candida internal control (IC) nucleic acid that is amplified and detected in the same assay reaction mixtures by using amplification and detection oligomers specific for the IC sequence. Amplification and detection of a signal from the amplified IC sequence demonstrates that the assay reagents, conditions, and procedural steps were properly used and performed in the assay if no signal is obtained for the intended target *Candida* nucleic acid (e.g., samples that provide negative results for *C. albicans*). The IC may be used as an internal calibrator for the assay when a quantitative result is desired, i.e., the signal obtained from the IC amplification and detection is used to set a parameter used in an algorithm for quantitating the amount of *Candida* nucleic acid in a sample based on the signal obtained for amplified an *Candida* target sequence. A preferred IC embodiment is a randomized sequence that has been derived from a naturally occurring source (e.g., an HIV sequence that has been rearranged in a random manner). A preferred IC may be an RNA transcript isolated from a naturally occurring source or synthesized in vitro, such as by making transcripts from a cloned randomized sequence such that the number of copies of IC included in an assay may be accurately determined. The primers and probe for the IC target sequence are designed and synthesized by using any well known method provided that the primers and probe function for amplification of the IC target sequence and detection of the amplified IC sequence using substantially the same assay conditions used to amplify and detect the *Candida* target sequence and the IC components in the assay do not interfere with those used to amplify and detect the *Candida* target sequence. In preferred embodiments that include a target capture-based purification step, a target capture probe specific for the IC target is included in the target capture step so that the IC is treated in the same conditions as used for the intended *Candida* analyte in all of the assay steps.

EXAMPLES

For amplification and detection of target sequences in 26S rRNA sequences (which include 26S rRNA and DNA encoding 26S rRNA) of *Candida albicans*, oligomers were designed that act as amplification oligomers and detection probes by comparing known sequences of 26S rRNA or gene sequences encoding 26S rRNA and selecting sequences that are common to *C. albicans* isolates, but preferably are not completely identical to 26S rRNA sequences of other *Candida* species or other eukaryotic organisms. Sequence comparisons were conducted by using known 26S rRNA sequences (rRNA or genes) of *Candida* species (*C. dubliniensis, C. tropicalis* and *C. glabrata*) and of other fungal species (*S. cerevisiae, S. barnettii, S. exiguus, S. spencerorum, K. lodderae, S. rosinii, S. unisporus, S. servazzil, K. africanus, S. dairenensis, S. castellii, S. paradoxus, S. bayanus, K. yarrowii, K polysporus, E. gossypil* and *E. fibuliger*). Specific oligonucleotide sequences were selected, synthesized in vitro and characterized with purified rRNA from fungi using standard laboratory methods. The selected oligomers were further tested by using different combinations of the amplification oligomers in amplification reactions with whole cell lysates or total RNA purified from fungi grown in culture, to determine the relative efficiencies of amplification of the target sequences by using the selected amplification oligomers. The efficiencies of different combinations of oligomers were monitored by detecting the amplified products of the amplification reactions; generally by binding a labeled probe oligomer to the amplified products and detecting a signal that indicated the presence of amplified product.

Preferred embodiments of the selected amplification oligomers for *C. albicans* 26S rRNA target sequences are shown in Table 1. Amplification oligomers include those that may function as primers, promoter-primers, and/or promoter-provider oligomers. For the latter two, promoter sequences are shown in lower case in Table 1. Some oligomer embodiments include only the target-specific sequence of a corresponding promoter-primer or promoter-provider oligomer, e.g., SEQ ID NO: 4 is a target-specific sequence that is identical to the target-specific sequence contained in SEQ ID NO: 5, which includes a 5' promoter sequence. Those skilled in the art will appreciate that the target-specific sequences listed in Table may optionally be attached to the 3' end of any known promoter sequence to function as a promoter-primer or promoter-provider with the appropriate RNA polymerase for the chosen promoter sequence. An example of a promoter sequence specific for the RNA polymerase of bacteriophage T7 is SEQ ID NO: 37 (AATTTAATACGACTCACTATAGGGAGA). Preferred embodiments of amplification oligomers may include a mixture of DNA and RNA bases, and 2' methoxy RNA groups, e.g., oligomers of SEQ ID NOs: 1-3 and 19-21 may include RNA bases and 2' methoxy linkages at the first four positions from the 5' end. Embodiments of amplification oligomers may be modified by synthesizing the oligomer with the 3' end blocked to make the oligomer optimal for functioning as a blocking molecule or promoter-provider oligomer in a single-primer transcription-associated amplification reaction. Preferred embodiments of 3'-blocked oligomers include those of SEQ ID NOs: 5, 7, 9, 16-18, 23, 25, 27 and 32-34 that include a blocked C near or at the 3' end.

Preferred embodiments of the selected detection probe oligomers for detecting amplified products of 26S rRNA sequences or DNA encoding 26S rRNA are shown in Table 2. Preferred detection probe embodiments are oligomers that form hairpin configurations by intramolecular hybridization of the probe sequence, of which preferred embodiments are those of SEQ ID NOs: 11, 13, 15, 29 and 31. Preferred hairpin probe oligomers are synthesized with a fluorescent label attached at one end and a quencher compound attached at the other end of the sequence. Embodiments of hairpin probes may be labeled with a 5' fluorophore and a 3' quencher, e.g., 5' fluoroscein label with 3' DABCYL quencher. Some embodiments of hairpin oligomers include a non-nucleotide linker moiety at selected positions within the sequence, e.g., oligomers that include an abasic 9-carbon ("C9") linker located in: SEQ ID NO: 11 between nt 5 and nt 6, SEQ ID NO: 13 between nt 20 and nt 21, SEQ ID NO: 15 between nt 17 and nt 18, SEQ ID NO: 29 between nt 16 and nt 17, and SEQ ID NO: 31 between nt 20 and nt 21.

TABLE 1

| Sequence | SEQ ID NO. |
| --- | --- |
| CAGATTCCCCTTGTCCGTACC | 1 |
| GACAGTCAGATTCCCCTTGTCC | 2 |
| CACUTTCTGACCATCACAATGC | 3 |
| GATAAGGATTGGCTCTAAGGATCGGGTGTC | 4 |
| aatttaatacgactcactatagggagaGATAAGGATTGGCTCTAAGGATCGGGTGTC | 5 |
| GCGGTGACTGTTGGCGGGCTGTTTC | 6 |
| aatttaatacgactcactatagggagaGCGGTGACTGTTGGCGGGCTGTTTC | 7 |
| GCTGTTTCACGACGGACTGCTGGTGGATG | 8 |
| aatttaatacgactcactatagggagaGCTGTTTCACGACGGACTGCTGGTGGATG | 9 |
| CUUAUCCCGAAGUUACGGAUC | 16 |
| CACCGCCGCGUCUACACAAG | 17 |
| GAAACAGCCCGCCAACAGUCAC | 18 |
| CCUGCGUUAUCGUUUAACAGAUGUGCC | 19 |
| CAUGAGUCCCCCUUAGGACACCUGC | 20 |
| GGAGATTTCTGTTCTCCATGAGTCC | 21 |
| GGAGGGTGTAGAATAAGTGGGAGCTTCG | 22 |
| aatttaatacgactcactatagggagaGGAGGGTGTAGAATAAGTGGGAGCTTCG | 23 |
| GCTTCGGCGCCGGTGAAATACCACTACC | 24 |
| aatttaatacgactcactatagggagaGCTTCGGCGCCGGTGAAATACCACTACC | 25 |
| CTTATTCAATGAAGCGGAGCTGGAGGTC | 26 |
| aatttaatacgactcactatagggagaCTTATTCAATGAAGCGGAGCTGGAGGTC | 27 |
| CCUCCAUGUCUUUUCACAAUG | 32 |
| GAAGCUCCCACUUAUUCUAC | 33 |
| GAAUAAGUAAAAAAACUAUAG | 34 |

TABLE 2

| Sequence | SEQ ID NO. |
| --- | --- |
| CCAUAAAGACCUACCAAGCGUG | 10 |
| cacgcCCAUAAAGACCUACCAAGCGUG | 11 |
| CCGGACGGCCAUAAAGACCU | 12 |
| CCGGACGGCCAUAAAGACCUuccgg | 13 |
| CGGACGGCCAUAAAGAC | 14 |
| CGGACGGCCAUAAAGACguccg | 15 |
| CCCAGAGGGCUUAAUG | 28 |
| CCCAGAGGGCUUAAUGcuggg | 29 |
| CGGAUCGCCCAGAGGGCUUA | 30 |
| CGGAUCGCCCAGAGGGCUUAauccg | 31 |

Embodiments of non-specific and specific capture probe oligomers for use in sample preparation to separate *Candida* 26S rRNA target nucleic acids from other sample components include those that contain the sequences of SEQ ID NO: 35 (kkkkkkkkkkkkkkkkkk) and SEQ ID NO: 36 (CGAGGCAUUUGGCUACCUUAAGAG), respectively. Preferred embodiments of the capture probes include a 3' tail region covalently attached to the sequence to serve as a binding partner that binds a hybridization complex made up of the target nucleic acid and the capture probe to an immobilized probe on a support. Preferred embodiments of capture probes that include the sequences of SEQ ID NOs: 35 and 36 further include 3' tail regions made up of substantially homopolymeric sequences, e.g., a $dT_3A_{30}$ sequence.

Reagents used in target capture and amplification described in the examples herein generally include one or more of the following. Lysis Reagent: 20 mM Lithium Succinate, 0.1% (w/v) LLS, and 1 mM LiOH. Target Capture Reagent: 250 mM HEPES, 310 mM LiOH, 1.88 M LiCl, 100 mM EDTA, pH 6.4, and 250 µg/ml of paramagnetic particles (0.7-1.05µ particles, SERA-MAG™ MG-CM, Seradyn, Inc., Indianapolis, Ind.) with covalently bound $(dT)_{14}$ oligomers. Wash Solution: 10 mM HEPES, 150 mM NaCl, 6.5 mM NaOH, 1 mM EDTA, 0.3% (v/v) ethanol, 0.02% (w/v) methyl paraben, 0.01% (w/v) propyl paraben, and 0.1% (w/v) sodium lauryl sulfate, pH 7.5. Amplification reagent: 46.1 mM HEPES, 86.2 mM Trehalose Dihydrate, 33 mM KCl, 30.6 mM MgCl$_2$, 1.7 mM NaOH, 0.5 mM of each dNTP (dATP, dCTP, dGTP, dTTP), 10 mM rATP, 2 mM rCTP, 2 mM UTP, 12 mM rGTP, 0.4% ethanol, 0.1% methylparaben, 0.02% propylparaben. Enzyme Reagent: 58 mM HEPES, 3.03% (w/v) Trehalose Dihydrate, 50 mM N-acetyl-L-cysteine, 10% (v/v) Triton X-100, 1.04 mM EDTA Disodium Dihydrate, 20% Glycerol, 120 mM KCl, and about 360 RTU/μl of MMLV reverse transcriptase (MMLV-RT) and about 80 U/μl of T7 RNA polymerase. One reverse transcriptase unit ("RTU") of activity for MMLV reverse transcriptase is defined as the incorporation of 1 nmol dTMP into DE81 filter-bound product in 20 minutes at 37° C. using (poly(rA)-p(dT)$_{12-18}$) as the substrate, and for T7 RNA polymerase, one unit ("U") of activity is defined as the production of 5.0 fmol RNA transcript in 20 minutes at 37° C. All of the reagent addition and mixing steps may be performed manually, or by using a combination of manual and automated steps, or by using a completely automated system. Amplification methods that use single-primer transcription-associated amplification use procedures substantially as disclosed in US Pub. No. 2006-0046265 A1, Becker et al. Methods for using hairpin probes have been disclosed in detail in U.S. Pat. Nos. 6,849,412, 6,835,542, 6,534,274 and 6,361,945.

Different amplification oligomer combinations were made from those listed in Table 1 and were tested in single-primer transcription-associated amplifications as described above, using whole cell lysates or ribosomal RNA isolated from *C. albicans* and other fungi as target nucleic acid. Amplified products were detected by using hairpin probes (molecular torches) from those listed in Table 2 labeled with a fluorophore (5' fluorescein) and 3' quencher (DABCYL), detecting the fluorescence emitted when the probe bound to amplified sequences.

Example 1

Amplification and Detection Probe Oligomer Combinations

Amplification and detection of a *C. albicans* 26S rRNA target sequence was demonstrated in real-time by using a probe that hybridizes to the amplified product during the amplification reaction. Amplification was performed by using a single-primer transcription-associated amplification procedure substantially as described in detail in US Pub. No. 2006-0046265 A1, conducted by using some of the selected amplification oligomers. Each of the assays was performed in an amplification reaction (0.040 ml total volume) that contained the *C. albicans* target RNA and amplification reagents substantially as described for TMA reactions but with a promoter-provider oligomer (12 pmol per reaction), a primer oligomer (6 pmol per reaction), a blocker oligomer (0.5 pmol per reaction), and a hairpin probe (molecular torch at 6 pmol per reaction). Reaction mixtures containing the amplification oligomers, target and amplification reagents (but not enzymes) were covered to prevent evaporation, incubated 10 min at 60° C., then 5 min at 42° C., then enzymes were added (10 μl vol) and the reactions were mixed and incubated for 50 min at 42° C., measuring fluorescence every 20 sec during the amplification reaction after enzyme addition.

TABLE 3

| Oligomer Combinations SEQ ID NOs | Average Measured Time-of-Emergence (min) | | |
|---|---|---|---|
| | 0 copies/rxn | $3 \times 10^4$ copies/rxn | $3 \times 10^7$ copies/rxn |
| 1, 5, 11, 16 | ND | ND | 18.9 |
| 1, 5, 13, 16 | ND | ND | ND |
| 1, 5, 15, 16 | ND | ND | 18.6 |
| 2, 5, 11, 16 | ND | ND | 20.2 |
| 2, 5, 13, 16 | ND | ND | 19.8 |
| 2, 5, 15, 16 | ND | ND | 19.3 |
| 3, 5, 11, 16 | ND | ND | ND |
| 3, 5, 13, 16 | ND | ND | ND |
| 3, 5, 15, 16 | ND | ND | ND |
| 1, 7, 11, 17 | ND | 21.9 | 14.5 |
| 1, 7, 13, 17 | ND | 23.8 | 18.2 |
| 1, 7, 15, 17 | ND | 22.5 | 15.7 |
| 2, 7, 11, 17 | ND | 23.8 | 14.7 |
| 2, 7, 13, 17 | ND | 24.4 | 18.1 |
| 2, 7, 15, 17 | ND | 21.7 | 15.5 |
| 3, 7, 11, 17 | ND | ND | ND |
| 3, 7, 13, 17 | ND | ND | ND |
| 3, 7, 15, 17 | ND | ND | ND |
| 1, 9, 11, 18 | ND | 19.2 | 12.3 |
| 1, 9, 13, 18 | ND | 20.0 | 15.7 |
| 1, 9, 15, 18 | ND | 18.3 | 13.1 |
| 2, 9, 11, 18 | ND | ND | 13.2 |
| 2, 9, 13, 18 | ND | ND | 15.9 |
| 2, 9, 15, 18 | ND | ND | 13.6 |
| 3, 9, 11, 18 | ND | ND | ND |
| 3, 9, 13, 18 | ND | ND | ND |
| 3, 9, 15, 18 | ND | ND | ND |
| 19, 23, 29, 32 | ND | ND | ND |
| 19, 23, 31, 32 | ND | ND | ND |
| 20, 23, 29, 32 | ND | ND | ND |
| 20, 23, 31, 32 | ND | ND | ND |
| 21, 23, 29, 32 | ND | ND | ND |
| 21, 23, 31, 32 | ND | ND | ND |
| 19, 25, 29, 33 | ND | 19.7 | 15.0 |
| 19, 25, 31, 33 | ND | 24.8 | 21.1 |
| 20, 25, 29, 33 | ND | ND | 27.6 |
| 20, 25, 31, 33 | ND | ND | 30.0 |
| 21, 25, 29, 33 | ND | ND | 33.1 |
| 21, 25, 31, 33 | ND | ND | ND |
| 19, 27, 29, 34 | ND | 30.6 | 23.4 |
| 19, 27, 31, 34 | ND | 30.9 | 27.5 |
| 20, 27, 29, 34 | ND | ND | ND |
| 20, 27, 31, 34 | ND | ND | ND |
| 21, 27, 29, 34 | ND | ND | ND |
| 21, 27, 31, 34 | ND | ND | ND |

ND denotes not detected

Oligomer combinations SEQ ID NOs: 1, 7, 11 & 17, SEQ ID NOs: 2, 7, 11 & 17 and SEQ ID NOs: 19, 25, 29 & 33 showed the best sigmoidal curves at both 3×10$^4$ copies and 3×10$^7$ copies and clear distinction on emergence time between the two levels. No amplification was detected on any of the blanks (0 copies).

Example 2

Sensitivity

The preferred oligomer combinations from Example 1 were subsequently tested for *C. albicans* 26S rRNA target sensitivity.

TABLE 4

| | Average Measured Time-of-Emergence (min) | | |
|---|---|---|---|
| Target (copies/rxn) | Oligomer Combination SEQ ID NOs: 1, 7, 11, 17 | Oligomer Combination SEQ ID NOs: 2, 7, 11, 17 | Oligomer Combination SEQ ID NOs: 19, 25, 29, 33 |
| 0 | ND | ND | ND |
| 3 | ND | ND | ND |
| $3 \times 10$ | ND | ND | ND |
| $3 \times 10^2$ | 17.8 | 23.4 | 28.7 |
| $3 \times 10^3$ | 21.8 | 21.6 | 25.5 |
| $3 \times 10^4$ | 23.1 | 23.6 | 22.7 |
| $3 \times 10^5$ | 20.0 | 20.5 | 19.7 |
| $3 \times 10^6$ | 17.9 | 18.0 | 17.2 |

ND denotes not detected

Figure 2:
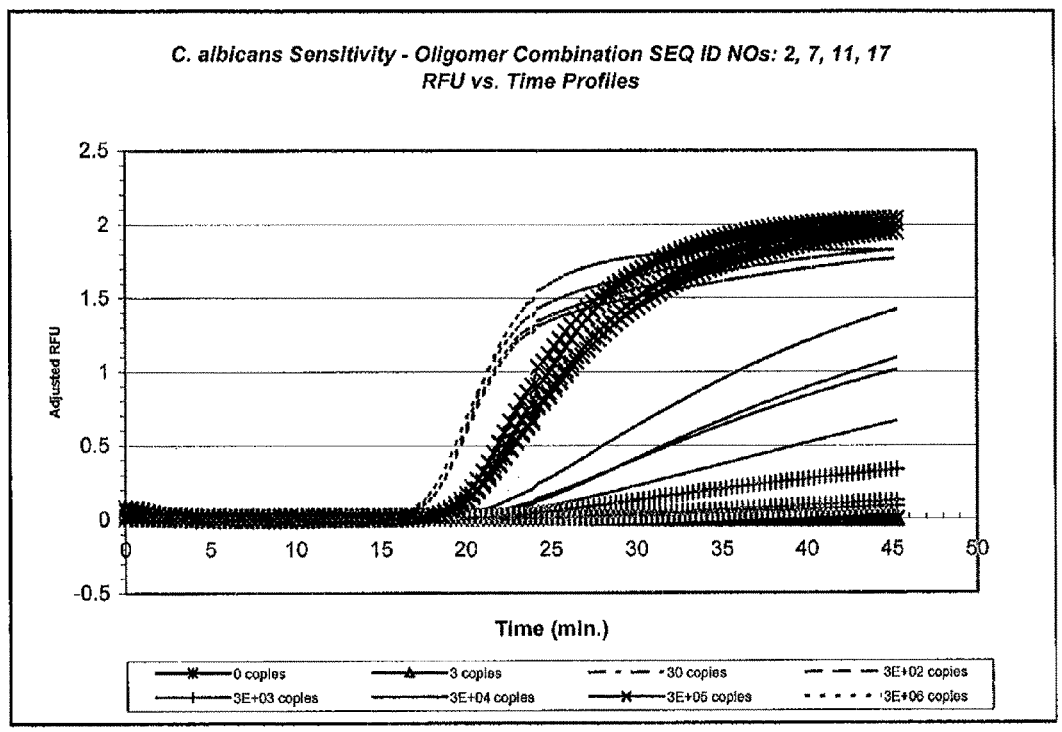
FIG. 2 shows the real-time fluorescent signal that was obtained from amplification of varying copy levels of *C. albicans* 26S rRNA using oligomer combination SEQ ID NOs: 2, 7, 11 & 17 as described in Example 2.
Figure 3:
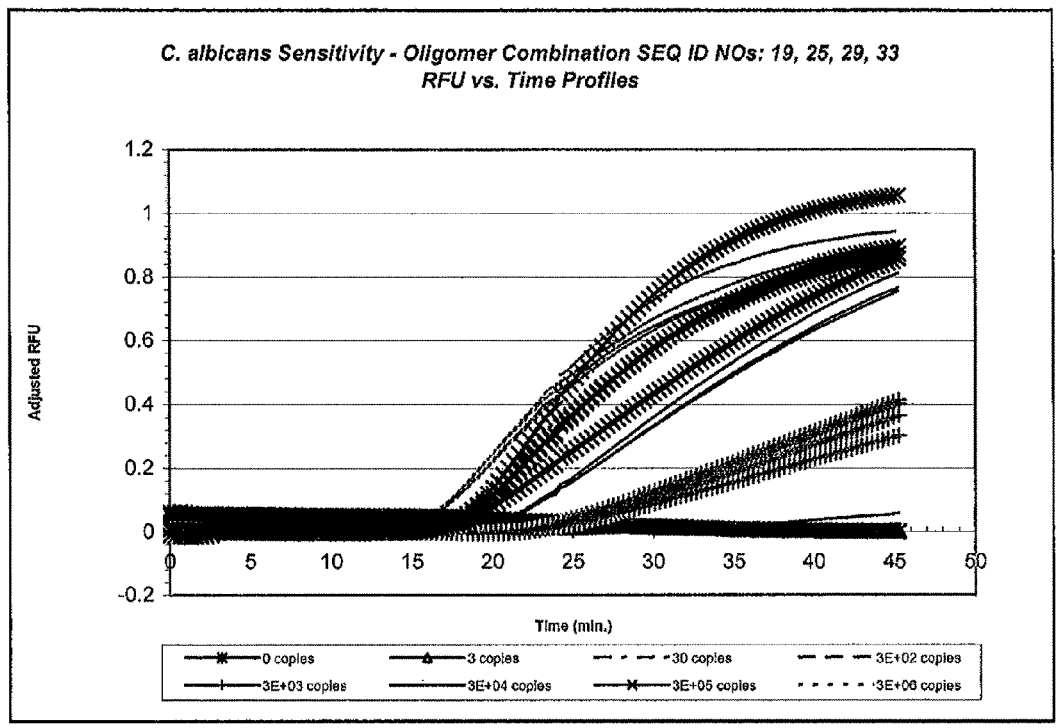
FIG. 3 shows the real-time fluorescent signal that was obtained from amplification of varying copy levels of *C. albicans* 26S rRNA using oligomer combination SEQ ID NOs: 19, 25, 29 & 33 as described in Example 2.

Referring to Table 4 in conjunction with FIGS. 1-3, all three oligomer combinations unequivocally detected down to at least $3 \times 10^4$ copies (approximately 3 cells). Oligomer combination SEQ ID NOs: 19, 25, 29 & 33 unequivocally detected down to $3 \times 10^3$ copies (approximately 0.3 cell).

Example 3

Specificity

Oligomer combinations SEQ ID NOs: 1, 7, 11 & 17 and SEQ ID NOs: 19, 25, 29 & 33 were also tested for *C. albicans* 26S rRNA target specificity.

TABLE 5

| | Oligomer Combination SEQ ID NOs: 1, 7, 11, 17 | | Oligomer Combination SEQ ID NOs: 19, 25, 29, 33 | |
|---|---|---|---|---|
| Organism | Target (copies/rxn) | Average Measured Time-of-Emergence (min) | Target (copies/rxn) | Average Measured Time-of-Emergence (min) |
| *C. albicans* | $3 \times 10^9$ | 15.4*/10.4** | $3 \times 10^9$ | 15.5*/9.9** |
| *C. guillermondii* | $3 \times 10^9$ | ND* | $3 \times 10^9$ | ND* |
| *C. kruseii* | $3 \times 10^9$ | ND* | $3 \times 10^9$ | ND* |
| *C. parapisilosis* | $3 \times 10^9$ | 15.2* | $3 \times 10^9$ | ND* |
| *C. tropicalis* | $3 \times 10^9$ | 15.0* | $3 \times 10^9$ | ND* |
| *C. glabrata* | $3 \times 10^9$ | 14.6** | $3 \times 10^9$ | ND** |
| *C. kefur* | $3 \times 10^9$ | 14.0** | $3 \times 10^9$ | ND** |

ND denotes not detected
*denotes result from 1st experiment
**denotes result from 2nd experiment Oligomer combination SEQ ID NOs: 19, 25, 29 & 33 demonstrated specificity for *C. albicans* without detection of *C. guillermondii, C. kruseii, C. parapisilosis, C. Tropicalis, C. giabrata* and *C. kefur*.

Example 4

Target Capture

Non-specific and specific target capture of *C. albicans* 26S rRNA were compared using oligomer combinations SEQ ID NOs: 1, 7, 11 & 17 and SEQ ID NOs: 19, 25, 29 & 33 for amplification and detection.

TABLE 6

| | Average Measured Time-of-Emergence (min) | | | |
|---|---|---|---|---|
| | Oligomer Combination SEQ ID NOs: 1, 7, 11, 17 | | Oligomer Combination SEQ ID NOs: 19, 25, 29, 33 | |
| Target (copies/rxn) | TC Oligomer SEQ ID NO: 35 | TC Oligomer SEQ ID NO: 36 | TC Oligomer SEQ ID NO: 35 | TC Oligomer SEQ ID NO: 36 |
| 0 | ND | 17.7 | ND | ND |
| $10^2$ | ND | 7.1 | 25.8 | 4.8 |
| $10^3$ | 11.2 | ND | 21.1 | 19.6 |
| $10^4$ | 11.7 | 20.8 | 18.5 | 17.9 |
| $10^5$ | 18.0 | 17.7 | 15.7 | 16.1 |
| $10^6$ | 16.5 | 15.9 | 14.2 | 14.1 |
| $10^7$ | 14.7 | 14.5 | 12.5 | 12.5 |
| $10^8$ | 12.9 | 12.9 | 11.0 | 10.9 |

ND denotes not detected

Non-specific and specific target capture demonstrated comparable performance. All oligomer combinations unequivocally detected down to $10^4$ copies (approximately 1 cell). Oligomer combination SEQ ID NOs: 19, 25, 29 & 33 unequivocally detected down to $10^3$ copies (approximately 0.1 cell).

The invention claimed is:

1. A set of oligomers for use in amplifying a *Candida albicans* 26S rRNA sequence or DNA encoding the 26S rRNA sequence, the set of oligomers comprising first and second amplification oligomers, wherein the first amplification oligomer consists of the base sequence of SEQ ID NO:19, the DNA equivalent of SEQ ID NO:19, or a combination RNA/DNA equivalent of SEQ ID NO:19, and wherein the second amplification oligomer is a promoter-primer comprising a 5' promoter sequence and a target binding region that consists of the base sequence of SEQ ID NO:24, the DNA equivalent of SEQ ID NO:24, or a combination RNA/DNA equivalent of SEQ ID NO:24.

2. The set of oligomers of claim 1, further comprising a probe up to 50 bases in length and comprising a target binding sequence that includes at least 10 contiguous bases of the base sequence of SEQ ID NO:28, the DNA equivalent of SEQ ID NO:28, or a combination RNA/DNA equivalent of SEQ ID NO:28.

3. The set of oligomers of claim 2, wherein the target binding sequence of the probe comprises the base sequence of SEQ ID NO:28, the DNA equivalent of SEQ ID NO:28, or a combination RNA/DNA equivalent of SEQ ID NO:28.

4. The set of oligomers of claim 3, wherein the base sequence of the probe consists of the base sequence of SEQ ID NO:29, the DNA equivalent of SEQ ID NO:29, or a combination RNA/DNA equivalent of SEQ ID NO:29.

5. The set of oligomers of claim 2, wherein the target binding sequence of the probe comprises the base sequence of SEQ ID NO:30, the DNA equivalent of SEQ ID NO:30, or a combination RNA/DNA equivalent of SEQ ID NO:30.

6. The set of oligomers of claim 5, wherein the base sequence of the probe consists of the base sequence of SEQ ID NO:31, the DNA equivalent of SE ID NO:31, or a combination RNA/DNA equivalent of SEQ ID NO:31.

7. The set of oligomers of claim 2, wherein the probe comprises a label.

* * * * *